United States Patent [19]
Moroz

[11] Patent Number: 5,871,735
[45] Date of Patent: Feb. 16, 1999

[54] ISOFERRITIN AS A MARKER FOR PATHOLOGICAL PREGNANCY

[76] Inventor: Chaya Moroz, 40 Yehuda Hanasi St., Tel Aviv, Israel, 69393

[21] Appl. No.: 536,832

[22] Filed: Jun. 12, 1990

Related U.S. Application Data

[60] Division of Ser. No. 210,601, Jun. 23, 1988, Pat. No. 4,954,434, which is a continuation-in-part of Ser. No. 179,183, Apr. 8, 1988, abandoned, which is a continuation-in-part of Ser. No. 164,947, Mar. 7, 1988, abandoned, which is a continuation of Ser. No. 568,275, Jan. 4, 1984, abandoned, which is a continuation-in-part of Ser. No. 373,715, Apr. 30, 1982, abandoned.

[30] Foreign Application Priority Data

May 15, 1981 [IL] Israel ............................................ 62879

[51] Int. Cl.$^6$ ...................... A61K 39/395; C07K 16/00; C07K 14/00
[52] U.S. Cl. ...................... 424/145.1; 514/8; 530/387.1; 530/400; 530/350; 530/388.24; 530/389.2; 435/336
[58] Field of Search ................................ 424/85.8, 145.1; 530/387, 400, 350, 388.24, 389.2; 435/336; 514/8

[56] References Cited

U.S. PATENT DOCUMENTS 4,882,270 11/1989 Moroz .
4,954,434 9/1990 Moroz .

OTHER PUBLICATIONS

Moroz et al., Clin. Chem. Acta, 148:111–118, 1985.
Sirota et al., Clin. Exp. Immunol., 76:1–6, 1989.
Kimmel et al J. Neurosurg 66:161–171 1987.
Harris et al TibTech 11:42–46 1993.

*Primary Examiner*—F C Eisenschenk
*Attorney, Agent, or Firm*—Pennie & Edmonds LLP

[57] ABSTRACT

The present invention relates to a method of diagnosis of pathological pregnancy which relies on an evaluation of the amount of placental isoferritin (PLF) in the serum or amniotic fluid of a pregnant woman. Diagnosis may also be achieved by observation of percentages of PLF-bearing lymphocytes in the pregnant female. Detection of PLF levels is achieved by immunoassay with a PLF-specific antibody. Also described is a method of treating or preventing pathological pregnancies and transplant or graft rejection by administration of effective amounts of PLF and/or a PLF-specific antibody in combination with immunization.

11 Claims, 11 Drawing Sheets

| PLF / DELIVERY | + | % | – | % |
|---|---|---|---|---|
| TERM | 2 | 100% | 3 = | 37.5 |
| PRE-TERM | – | – | 5 = | 62.5 |

FIG. 3

ISOFERRITIN AS A MARKER FOR PATHOLOGICAL PREGNANCY

This application is a division of 07/210,601, filed Jun. 23, 1988, now U.S. Pat. No. 4,954,434, which is a continuation in part of 07/179,183, filed Apr. 8, 1988, now abandoned, which is a continuation in part of 07/164,947, filed Mar. 7, 1988, now abandoned, which is a continuation of 06/568,275, filed Jan. 4, 1984, now abandoned, which is a continuation in part of 06/373,715, filed Apr. 30, 1982, now abandoned.

TABLE OF CONTENTS
1. Field of the Invention
2. Background of the Invention
   2.1. Ferritin
       2.1.1. Placental Isoferritin
   2.2. Pathological Pregnancy
       2.2.1. Clinical Symptoms of Pathological Pregnancies
       2.2.2. Immunosuppression and Pregnancy
3. Summary of the Invention
4. Brief Description of the Figures
5. Detailed Description of the Invention
   5.1. Immunoassays
   5.2. Ferritin-Bearing Lymphocytes
   5.3. Immunosuppression Therapy
       5.3.1. PLF Therapy and Pregnancy
       5.3.2. PLF and Transplants
       5.3.3. Therapeutic Regimens
6. Example
   6.1. Preparation of Monoclonal Antibodies
       6.1.1. Preparation of Oncofetal Ferritin
       6.1.2. Preparation of Non-PLF Specific Hybridomas
       6.1.3. Preparation of PLF-Specific Hybridomas
   6.2. PLF Levels and Preterm Deliveries
   6.3. PLF Levels and Toxemia of Pregnancy

FIELD OF THE INVENTION

There is currently a widespread need for simple yet accurate means of diagnosis for a number of conditions which affect pregnant women. It is often difficult, if not impossible, to determine in advance which pregnant women are at risk for certain conditions which may prevent carrying a child to term, and/or which may endanger the life of both mother and fetus. Early detection of problem pregnancies enables rapid implementation of necessary therapy or prophylactic measures. The present invention now provides a serum marker which may be used for the diagnosis and detection of several types of pathological pregnancies. The marker which is indicative in all these conditions is placental isoferritin (PLF; or oncofetal or embryonic ferritin). Accurate detection of the presence or absence of the marker is enabled by the discovery of a PLF-specific monoclonal antibody, as well as a broadly cross-reacting monoclonal antibody to isoferritin. The existence of these antibodies has made possible the construction of immunoassays which can accurately and rapidly facilitate diagnosis of the aforementioned disease states.

BACKGROUND OF THE INVENTION
2.1. FERRITIN

Iron is known to be an essential element of the makeup of every living organism, but may also become toxic at physiological pH values by virtue of its tending to oxidize, hydrolyze and precipitate as insoluble ferric oxide polymers. The protein ferritin, found in all living cells, is the body's means for ensuring that iron toxicity does not occur. Ferritin functions by storing iron in the cells in a soluble and readily available form. The iron stored in cells may then be mobilized whenever needed by the body, for example, for erythropoiesis.

The name "ferritin" actually encompasses a number of individual isomeric forms which are characteristic of different tissue types. Each isoferritin has 24 subunits of two distinct types, namely light subunits (L) and heavy subunits (H). These subunits differ in molecular weight, the light subunit being about 18 kDa, and the heavy subunit about 19–21 kDa. The isoferritins extracted from different tissues or organs typically exhibit different isoelectric points, with the isoelectric focusing pattern of human tissues forming a continuous spectrum; those tissues associated with high iron storage have ferritins at the basic end of the spectrum (e.g. spleen and liver), while iron poor tissues, (e.g. heart and placenta) and malignant cells have acidic ferritins. (Drysdale, *Ciba Found. Symp.* 51:41, 1977). The difference in isoelectric point appears to be related to the different distribution of light and heavy subunits in each type. Specifically, heavy subunit-rich ferritins are relatively acidic, and light chain rich ferritins are relatively basic (Cosell, et al., in *Ferritins and Isoferritins as Biochemical Markers*, p. 49–65, 1984, Elsevier). Current studies indicate that the H and L subunits are encoded by a complex group of genes, therefore suggesting that there is an even greater heterogeneity of ferritin molecules than had previously been expected.

2.1.1. PLACENTAL ISOFERRITIN

A specific type of acidic isoferritin has been shown to be characteristic of neoplastic cells and placental cells (Drysdale and Singer, *Cancer Res.* 44:3352, 1974). This protein is also known as oncofetal ferritin or placental isoferritin (PLF). Human placental ferritin has been shown to be composed predominantly of a single subunit type comigrating with a liver ferritin standard on SDS-PAGE (Brown et al. *Biochem. J.* 182:763, 1979). However, an immunoradiometric assay performed with anti-human spleen ferritin has shown tissue specific antigenicity for PLF. (Brown et al., supra). A three subunit structure has been revealed for PLF (Moroz et al. *G.I. Pat. Clin.* 1:17–23, 1986). In addition to the L and H subunits characteristic of all ferritins, there is also a high molecular weight (43 kDa) subunit which appears to be unique for human placenta, and thus provides a potential site for identification of the placental isoferritin molecule as distinguished from any other type of ferritin.

2.2. PATHOLOGICAL PREGNANCY

While the majority of women who become pregnant have no substantial difficulty in carrying a child to term, there are certain conditions which commonly arise in connection with problem pregnancies. Certain visible abnormalities, such as bleeding, may be symptomatic of more serious problems, but may also be a mere irregularity which does not develop into a condition which threatens the normal pattern of gestation. On the other hand, certain conditions such as spontaneous abortion, may occur without any warning, resulting in premature termination of the pregnancy and often in the death of the fetus. Although some women, in successive pregnancies, show a pattern of difficulty with carrying a fetus to term, and can therefore be treated accordingly in advance, the development of problems is not uniformly predictable, particularly in a first pregnancy. The early identification of a woman in a high risk category would facilitate prescription of an appropriate treatment regimen, thereby increasing the chances of full-term birth of a healthy baby, as well as decreasing the possible dangers to the mother's health. Some of the more commonly occurring problems during pregnancy are toxemia, premature contractions, premature delivery, missed abortion, and spontaneous abortions or miscarriages.

2.2.1. CLINICAL SYMPTOMS OF PATHOLOGICAL PREGNANCIES

A substantial number of pregnant women, perhaps as high as 7%, experience rapid weight gain, edema, and elevation of blood pressure at some time during their pregnancy. This condition, known as toxemia, results in a decrease in blood flow and in glomerular filtration, a situation which is completely the reverse of what is observed in a normal pregnancy. Because of the reduction in the glomerular filtration rate, the major problem is water retention. A particularly severe form of toxemia, eclampsia, is characterized by extreme vascular spasticity throughout the body, and clonic convulsion, followed by greatly decreased kidney output, hypertension and a general toxic condition. Toxemia of course threatens the health of the fetus, and in its more severe forms, may also threaten the mother's life.

Other problems may also arise during pregnancy which can be an indication of risk of premature delivery, or of spontaneous abortions. Many women may experience premature contractions at an early stage (as early as 16 weeks of gestation) during a pregnancy. The correlation of this symptom with a high risk of preterm delivery has not been clearly established. Similarly, abnormal bleeding can frequently occur at any time during pregnancy. This symptom may be an indication of an imminent miscarriage or a missed abortion; on the other hand, in about 50% of the cases it does not develop into anything more serious. Clearly, an early evaluation of such conditions, with some predictive significance as to risk of premature delivery or spontaneous abortion, would be of tremendous value to the clinician in both a hospital and office setting.

2.2.2. IMMUNOSUPPRESSION AND PREGNANCY

It has frequently been noted that something of an anomaly exists in a pregnancy being carried to full term: a fetal trophoblast which implants in the mother's uterus carries major histocompatibility antigens from both the mother and the father, and thus, except in rare circumstances, presents antigens to the maternal circulation (and immune system) which must, under normal circumstances, recognize the father's antigens as foreign. The embryo and fetus therefore stand in the position of an allograft, and, as yet, there has been no fully satisfactory explanation as to why the mother does not reject the fetus in much the same manner as a foreign skin graft would be rejected. It is clear that the embryo is protected in some way from the action of the mother's immune system. A number of mechanisms have been postulated to explain this phenomenon; among them are low levels or absence of Class II antigens on the syncytiotrophoblast which is in closest contact with the placenta, making it more likely that paternal Class I antigens will induce tolerance rather than a cytotoxic response; protection of trophoblast cells against cytotoxic lymphocytes by a barrier of negatively-charged mucopolysaccharide, or a protective effect of the physical barrier provided by the placenta.

Currently, one of the more popular theories of fetal protection is the suggestion of a general suppression of the mother's immune response. The placenta is known to secrete a variety of different products into the maternal circulation; these products include human chorionic gonadotropin (HCG) as well as substance known to have an immunoregulatory effect, such as estrogen, progesterone, corticosteroids, and pregnancy-associated growth factors (Caldwell et al. *J. Immunol.* 115:1249, 1975; Fabris et al. *Clin. Exp. Immunol.* 28:306, 1977; Baer et al. *Ciba Foundation Symp. Excerpts Medica* 64:293, 1979; Suteri et al. *Ann. NY Acad. Sci* 286:384, 1977; Monse et al. *J. Immunol.* 128:218, 1982). Placental isoferritin is also known to be secreted into the maternal circulation by the placenta (Brown et al. *Biochem. J.* 182:763, 1979). It has been suggested that some substance secreted by the placenta early in development may be responsible for inducing a general immunosuppression in the mother, thereby preventing rejection of the embryo and allowing normal full-term delivery.

In the same vein, a substantial number of irregularities which can occur during pregnancy also remain essentially unexplained as to cause. It has been suggested that some, or many of these problems may be associated with a mother's mounting an immunological response to the presence of foreign antigens on the fetus. In other words, in problem pregnancies, it is possible that the difficulties arise because of the failure of this postulated temporary immunosuppression to develop. The mother then reacts normally in response to a foreign stimulus, and various degrees of rejection of the fetus may then occur.

Evidence obtained in connection with the present invention provides the basis for suggestion of a mechanism for at least part of the physiological and immunological basis for tolerance (or non-tolerance) of the "fetal allograft" in pregnant women. It has now been discovered that a significant positive correlation exists between high serum PLF levels in pregnant women, and successful full term delivery. Similarly, abnormally low levels of PLF have been shown to be consistently associated with premature delivery, toxemia, and other pregnancy-related pathologies. Thus, low levels or absence of PLF in pregnant women can serve as marker for a potentially high risk pregnancy; detection of this state is ideally achieved by use of a PLF-specific monoclonal antibody in a novel immunoassay system, whereby early detection and diagnosis of a pathological condition can be made. This method is particularly well adapted for use in monitoring women after their first trimester of pregnancy, since levels of PLF, even in normal women, may be too low to detect prior to that time. For diagnosis of potential problems in first trimester, however, it has been discovered that detection of a relatively high level of ferritin bearing lymphocytes (FBL's) indicative of the occurrence of immunosuppression. Thus, pregnant women in the first trimester having less than about 5% of FBLs can be identified as potentially being at risk for a problem pregnancy.

The role of PLF in pregnancy does not appear to be limited to its use as a convenient marker however; there is also ample evidence to show that PLF plays an active role in the immunosuppression which appears to be a necessary event to support a normal pregnancy. Based on the observation of an apparent cause-and-effect relationship between PLF levels and immunosuppression, there is thus provided a means for treatment and prevention of actual and potentially pathological pregnancies, as well as a means for inducing immunosuppressions in those clinical situations in which production of a hyporesponsive immune state is desirable, e.g., in organ or tissue transplantation, to prevent rejection of the transplant.

3. SUMMARY OF THE INVENTION

The present invention relates to a method of detecting a pathological pregnancy which comprises contacting serum of a pregnant female with a first antibody capable of reacting with placental isoferritin (PLF) or normal serum ferritin, and a second antibody having specificity for placental isoferritin, said second antibody being linked to a reporter molecule capable of producing a detectable signal; allowing time sufficient for an antibody-PLF-antibody complex to form; observing the presence or absence of the detectable signal; and quantifying the result to determine the amount of placental isoferritin in the serum. Lower than normal amounts of placental isoferritin indicate risk of an abnormal pregnancy. In a preferred embodiment, the antibodies are both monoclonal antibodies. Examples of such useful monoclonal antibodies are CM-G-8, a monoclonal antibody which is capable of reacting with any type of ferritin, and CM-H-9, a monoclonal antibody which is capable of reacting only with placental isoferritin. As employed herein, the phrase "capable of reacting with placental isoferritin" is intended to encompass any antibody which can so react, e.g., either a general, relatively broadly cross-reacting antibody which will react generally with all types of ferritins as well as placental isoferritin-specific antibodies. The present assay permits early diagnosis of problem pregnancies, even before any symptoms appear; the early diagnosis thereby allows immediate treatment of the individual at risk, thus reducing the chances of a premature termination of pregnancy, and possible death of the fetus. The invention also provides a method for detecting pathological pregnancies in early stages of pregnancy, before PLF levels are detectable even in normal pregnant women, by observing the concentration of ferritin-bearing lymphocytes in the blood. Low levels of these FBLs is an indication of a poorly developed immunosuppressed state, and thus, a potentially pathological pregnancy.

The present invention also provides a method for inducing immunosuppression in a host by an initial administration of alloantigens, to provoke an overall immune response, and proliferation of T cells, in particular, a specific subset of ferritin-bearing lymphocytes; this is followed by an infusion of PLF or an anti-PLF antibody, at periodic intervals, i.e., throughout the period during which immunsuppression is desired. The PLF aids in maintaining the immunosuppression, once proliferation of the proper subset of suppressor T-cells has been achieved. A therapeutic regimen of this sort is particularly useful in the treatment of pathological pregnancies, as well in association with organ and tissue transplants.

4. BRIEF DESCRIPTION OF THE FIGURES

FIG. 3 shows an analysis of the delivery times of the same subjects plotted in FIG. 2; "+" indicates normal level of PLF, and "−" indicates low levels or no PLF.

Figure 5:
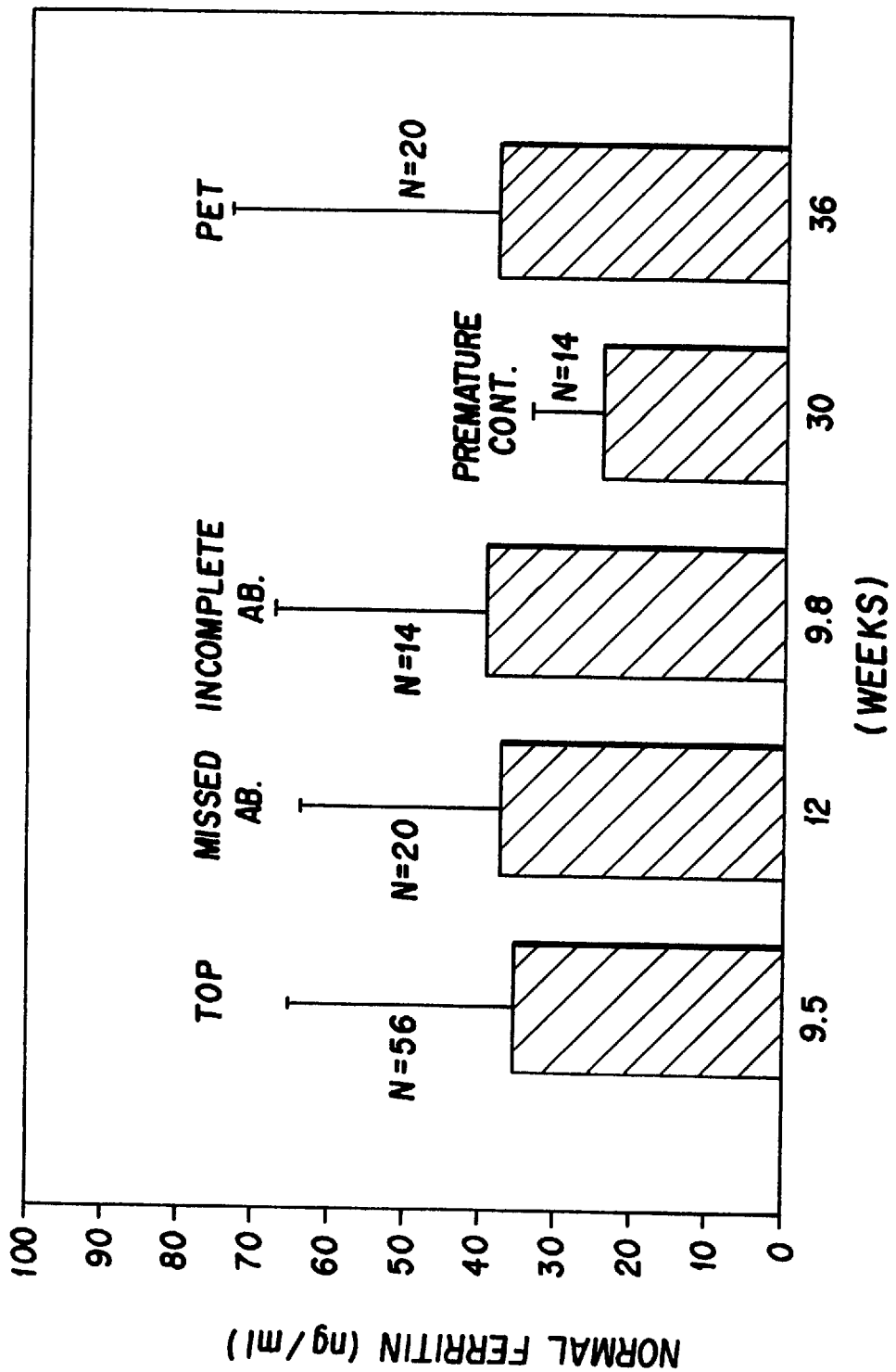

FIG. 5 shows a comparison of serum ferritin levels in women having normal pregnancies with women experiencing abnormal or pathological pregnancies. TOP=termination of pregnancy (voluntary abortion); PET=toxemia.

Figure 6:
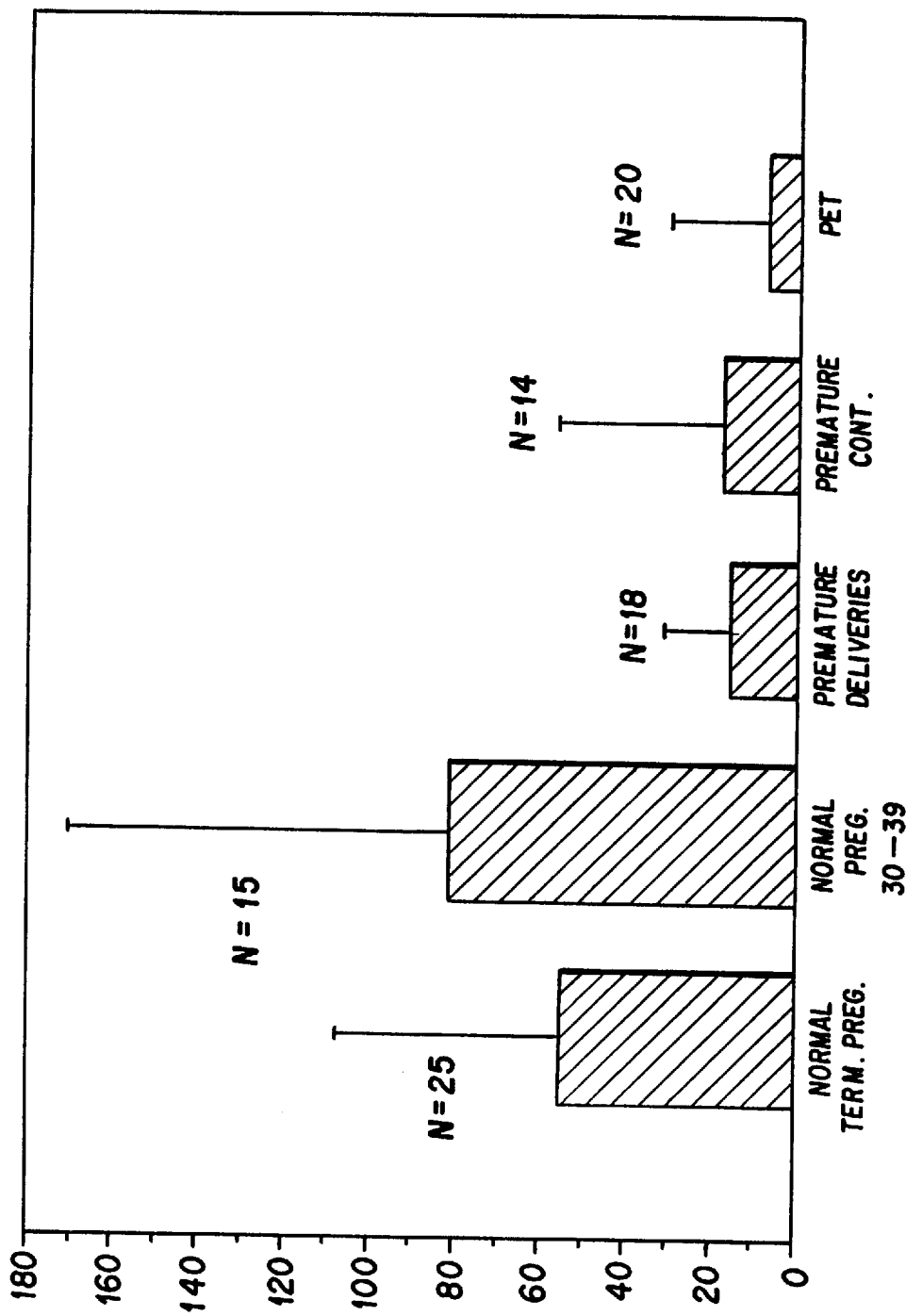

FIG. 6 shows a comparison of PLF levels on the third trimester of women having normal pregnancies with women experiencing abnormal or pathological pregnancies; PET= toxemia.

FIG. 7 shows levels of inhibition of immune response caused by addition of PLF, and/or PLF specific antibody to one way mixed lymphocyte cultures, compared with inhibition by a non-PLF specific antibody (CM-G-8) and normal ferritin (SPL-FER).

Figure 8:
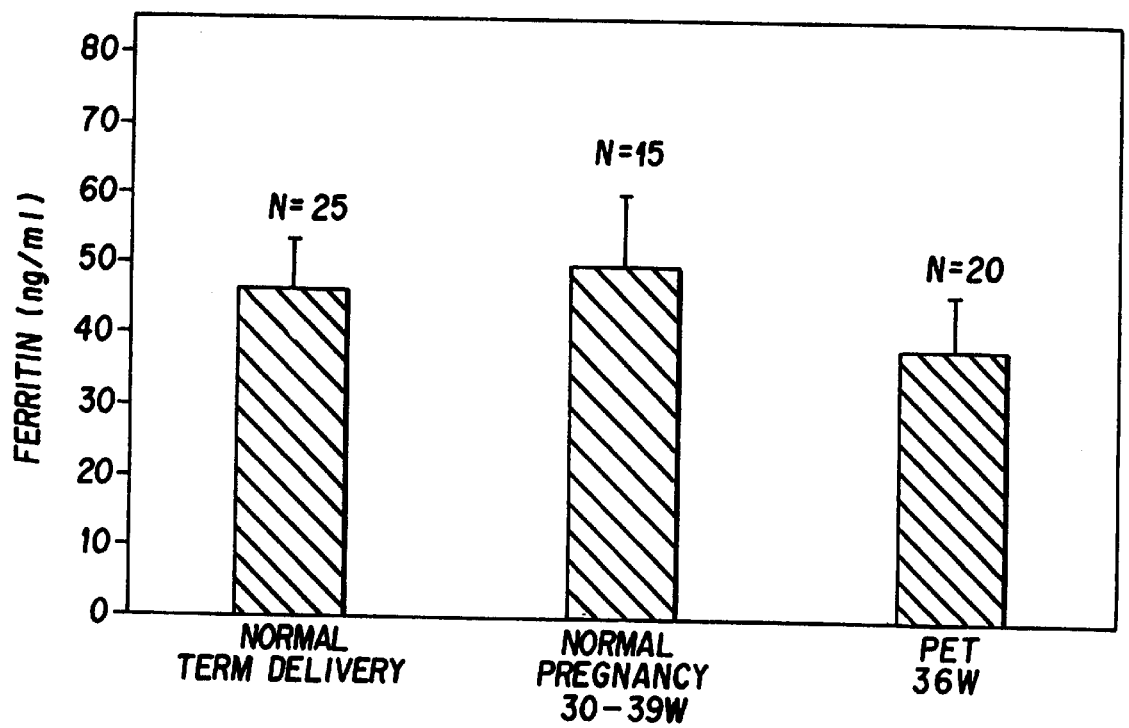

FIG. 8 shows a comparison of mean serum (normal) ferritin levels in women having a normal term delivery, women with a normal pregnancy at 30–39 weeks of gestation, and women with toxemia of pregnancy at 36 weeks of gestation.

Figure 9:
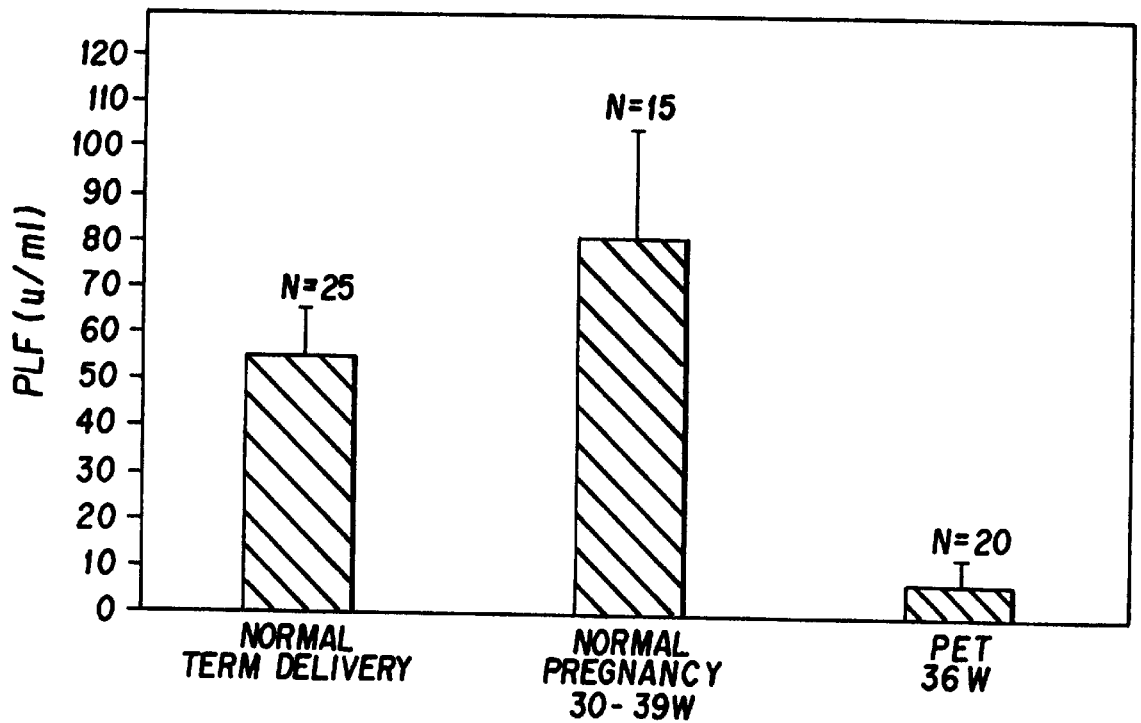

FIG. 9 shows a comparison of mean serum PLF levels among the same groups described in FIG. 8.

Figure 10:
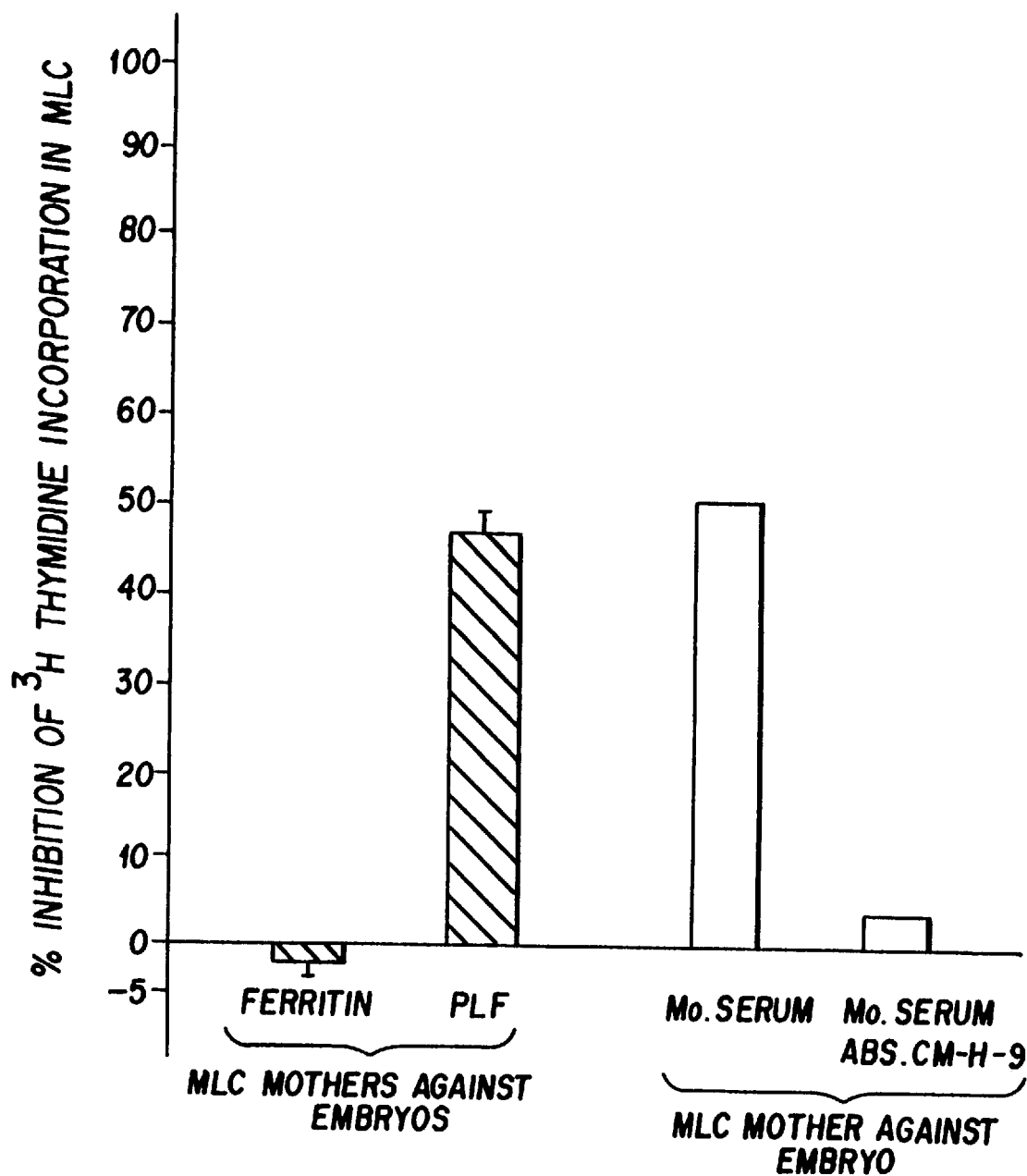

FIG. 10 shows a comparison of the inhibitory effect of untreated maternal serum, and maternal serum treated with an anti-PLF antibody on proliferation of T-cells in a one-way mixed lymphocyte reaction between maternal and embryo lymphocytes.

Figure 11:
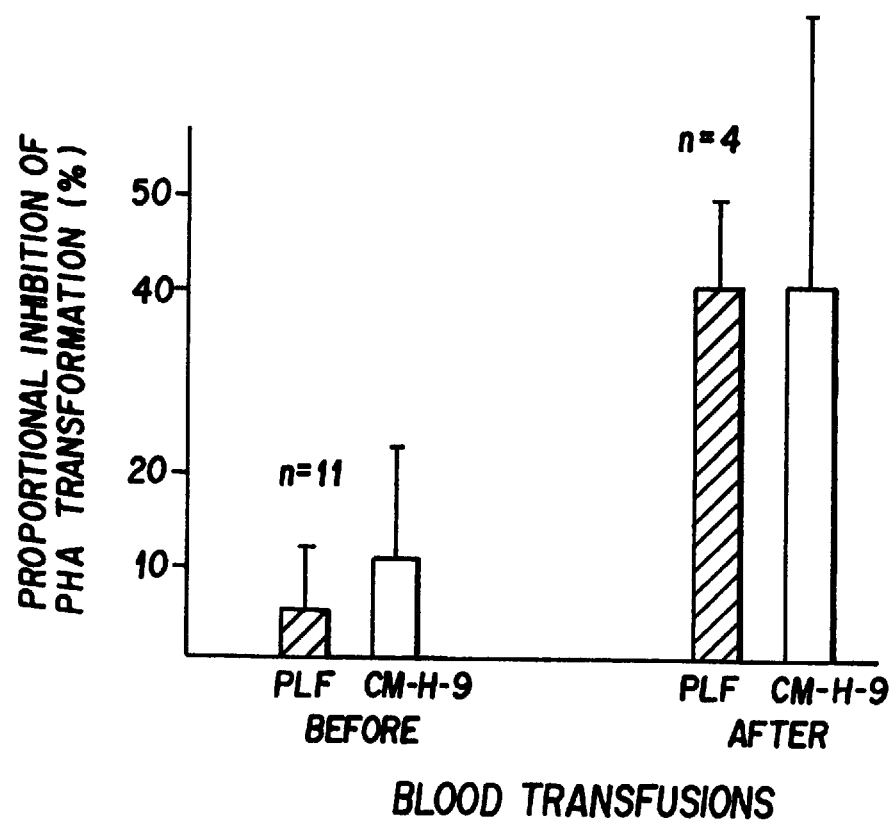

FIG. 11 shows a comparison of the inhibitory effects of PLF and anti-PLF antibody, on PHA induced proliferation of lymphocytes, both before and after transfusion.

5. DETAILED DESCRIPTION OF THE INVENTION

The present invention provides a means and a method by which placental isoferritin can be readily measured in serum. The observation that lower than normal levels of PLF in serum of a pregnant woman appears to be indicative of potential risk in pregnancy, in combination with the discovery of PLF-specific antibodies, is the basis for construction of immunoassays useful in the detection of PLF.

Figure 1:
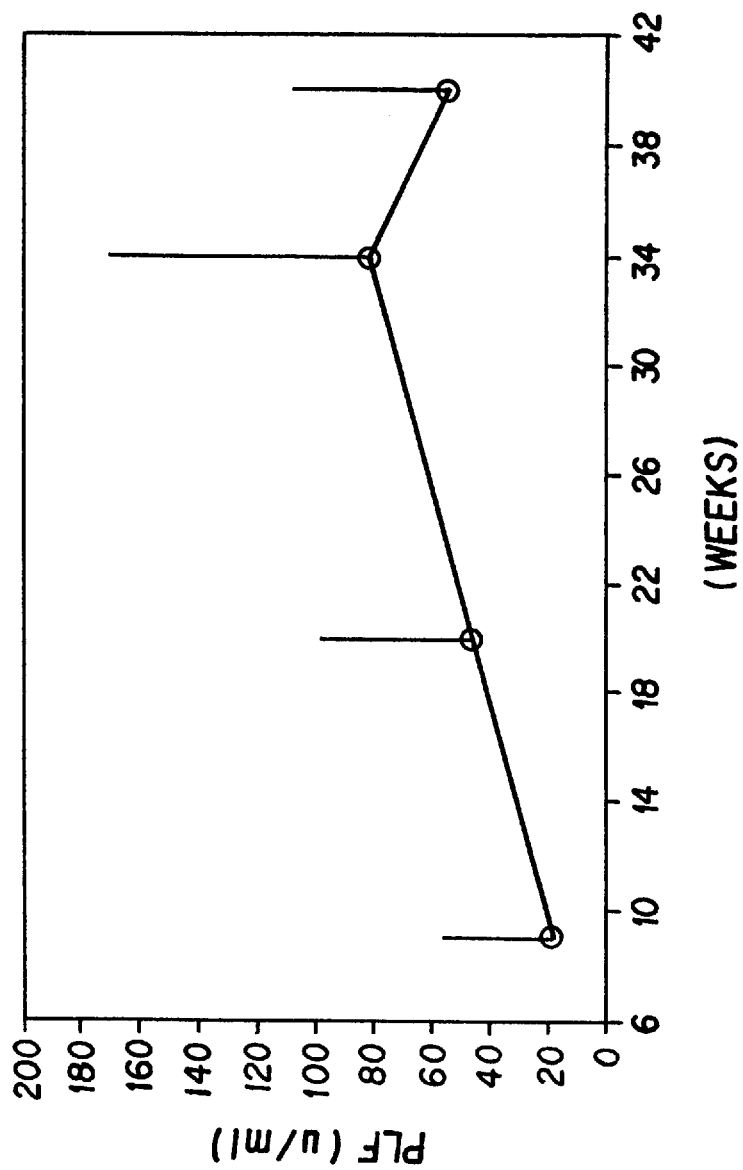
FIG. 1 shows a graphic depiction of the mean serum PLF levels throughout the course of pregnancy in normal pregnant women.

The level of PLF in normal, non-pregnant individuals is typically undetectable in their serum; on the other hand, elevated levels of PLF are routinely found in serum of healthy pregnant women (Moroz et al., Exp. *Haematol.* 15:258, 1987), from at least the 17th week of gestation, and perhaps earlier, up through full term delivery (FIG. 1). This level of PLF in pregnant women is independent of the total ferritin level observed. Unexpectedly, however, it has now been discovered that the levels of PLF in women exhibiting various types of irregularities or pathology in association with their pregnancy is exceptionally low or undetectable. This observation has repeatedly been made in significant numbers of women exhibiting clinical symptoms of toxemia, women who have delivered prematurely, women who have undergone spontaneous or missed abortions, and women who experience premature contractions and later deliver prematurely. The low levels of PLF in a pregnant woman can thus be employed as an accurate marker of a potentially pathological pregnancy, even before the onset of any clinical symptoms which would otherwise indicate. a problem existed.

Initial studies performed in connection with the present invention (Moroz et al. *Clin. Exp. Immunol.* 69:702–706, 1987) examined levels of PLF in the sera of several pregnant women, women at full-term, and preterm delivery, and their newborns. In the course of this study, a number of interesting observations came to light. Normal non-pregnant adult females have an average non-PLF normal ferritin level of about 50±59.8 ng/ml, but have very low or undetectable levels of placental ferritin in their blood, typically less than about 4.5±7.7 U/ml. The average amount of non-PLF ferritin does not really change significantly in pregnant women at any time during pregnancy. However, PLF levels increase significantly in pregnant women (see Table 1), reaching a peak just before delivery, and dropping back to normal levels shortly thereafter. Particularly surprising, however, was the observation that in mothers who delivered preterm newborns, the levels of PLF were significantly lower than observed in mothers who delivered full term newborns (see Table 2). Interestingly, the levels of PLF in both full-term and preterm newborns did not differ significantly.

Further clinical studies have now indicated that this observed pattern of reduced PLF levels is common to a number of other conditions characteristic of abnormal pregnancy. Studies on women with preclamptic toxemia of pregnancy (P.E.T.), when compared with non-toxemic pregnant women at similar stages of gestation, showed a pattern of reduced or undetectable PLF throughout pregnancy. Again, non-PLF ferritin levels were substantially identical for both groups of pregnant women (FIGS. 5 and 6).

Figure 2:
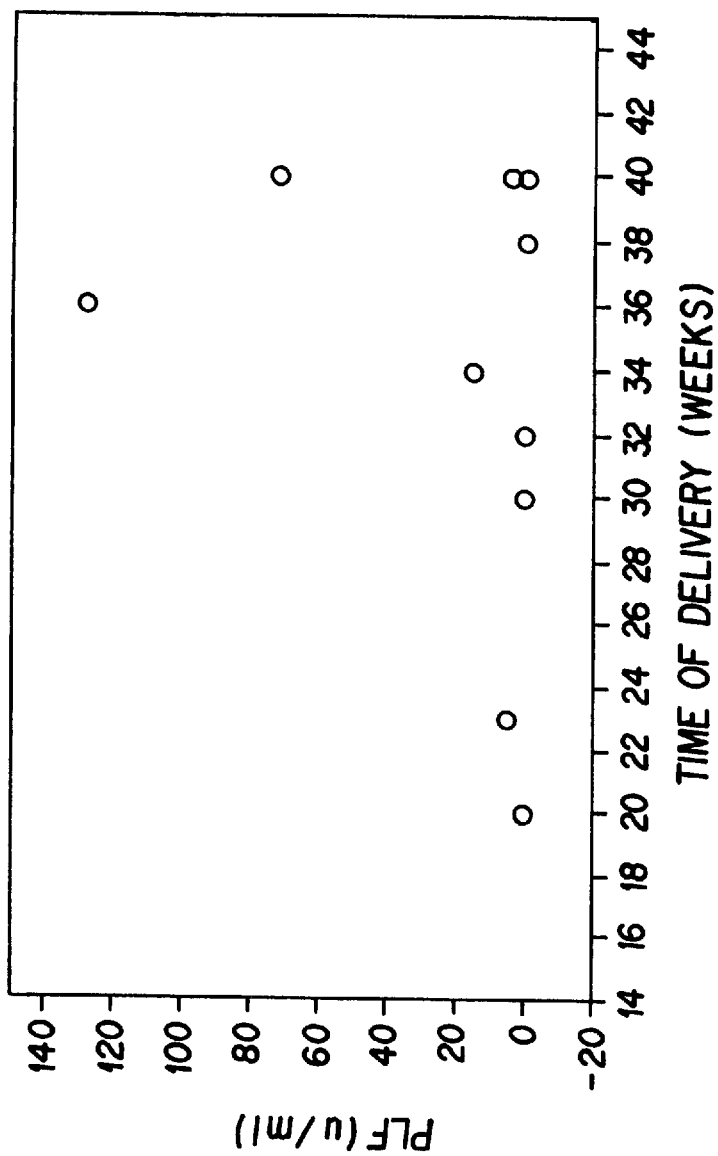
FIG. 2 shows a plot of serum PLF levels in pregnant women relative to the timing of their delivery.
Figure 3:
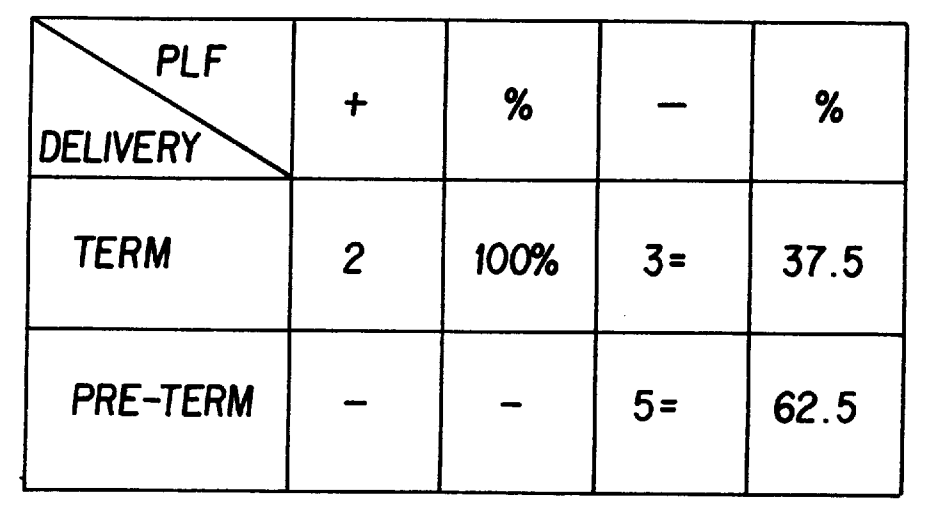
Figure 4:
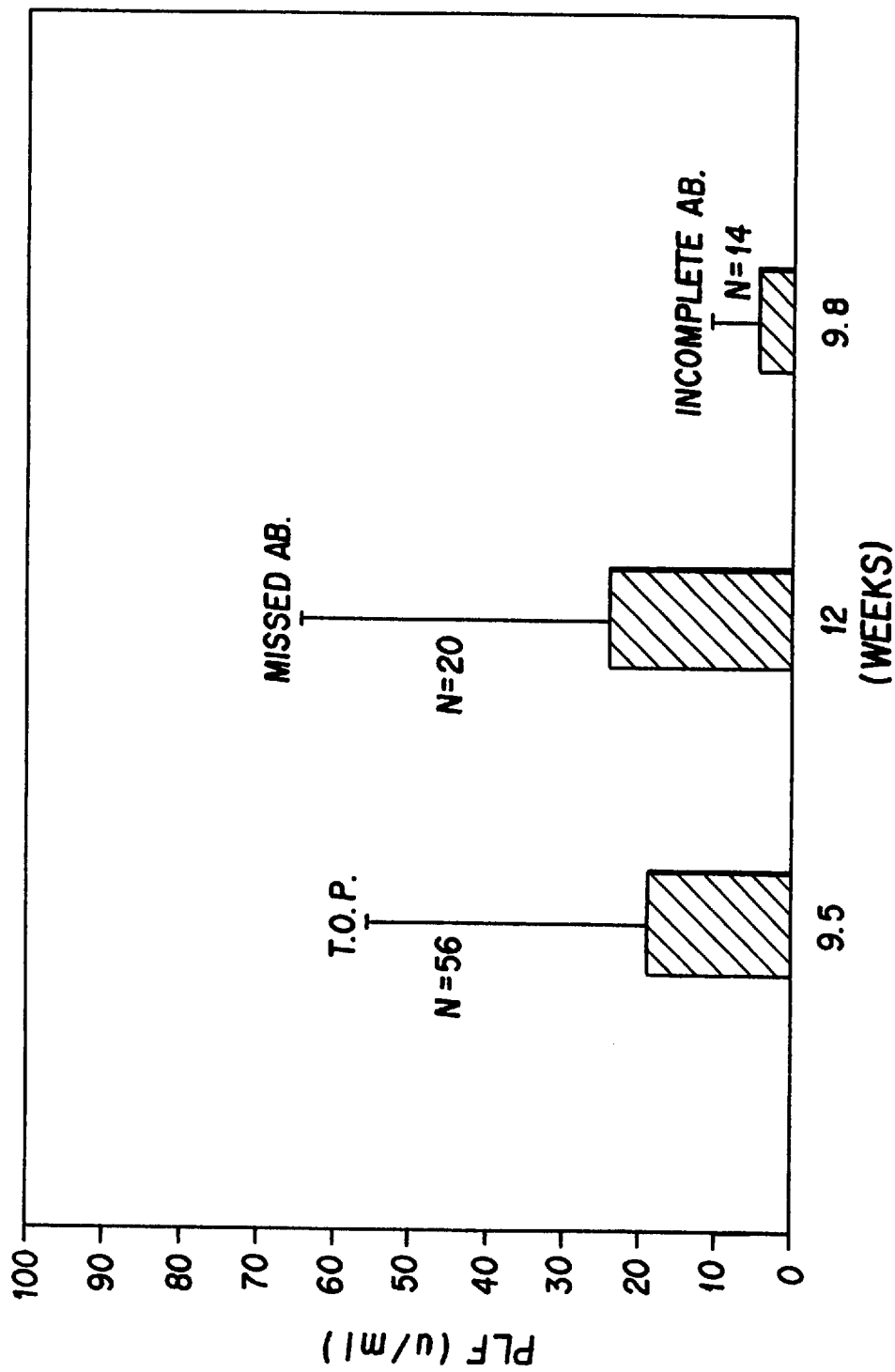
FIG. 4 shows a comparison of PLF levels in women experiencing spontaneous first trimester, missed abortions or incomplete abortions, with women having normal, voluntarily terminated pregnancies (TOP).

A third observation also correlates with the above findings. Clinical testing of serum of women who experience premature contractions early in pregnancy also suggests that low levels of PLF may be predictive of the occurrence of premature deliveries. Of the women selected for the trial, all of whom were experiencing premature contractions, a majority number showed PLF levels which were below normal for pregnant women. However, some of the women did show normal levels of PLF. Followup studies on all these women significantly showed that those showing normal levels of PLF did in fact carry their babies for the full term, whereas those women experiencing premature contractions with low PLF levels tended to deliver preterm infants. Thus, in conjunction with the occurrence of premature contractions, the level of PLF in pregnant women's serum appears to be indicative of a risk of premature delivery (see FIGS. 2 and 3). Finally, a significant number of women who spontaneously abort, or abort incompletely, have shown similar low levels of PLF (FIG. 4), while maintaining normal levels of non-PLF normal ferritin.

The foregoing observations establish a clear correlation between a low (i.e., less than 10 U/ml) level of PLF and high risk of an abnormal or pathological pregnancy. Thus, PLF can be used as an accurate marker for prediction of problem pregnancies, in many cases prior to the appearance of other clinical symptoms of pathology.

These observations concerning PLF levels as a prognostic indication have been successfully exploited in combination with novel immunoassays utilizing a PLF-specific monoclonal antibody. There are now available monoclonal antibodies which will react with PLF, but which will not react with any other type of ferritin. An example of a hybridoma producing such an antibody is deposited in the Institute Pasteur C.N.C.M. under Accession No. I-256, and the antibody is referred to herein as CM-H-9. A method for obtaining such antibodies is described in Section 6.2, infra. These antibodies may be used alone in a variety of different immunoassays in order to detect the levels of PLF present in the serum of pregnant women. Alternately, the PLF-specific antibodies may be used in combination with ferritin-specific but non-PLF specific antibodies. Monoclonal antibodies of this type are obtainable by the methods described in Section 6.1.2, infra, and are referred to herein as CM-G-8, or CM-OF-3; while these antibodies are produced by different clones, they apparently have the same specificity.

5.1. IMMUNOASSAYS

The present invention also provides a diagnostic assay for the detection of potentially problem pregnancies. The antibodies described above may be used as the basic reagents of a number of different immunoassays to determine the level of PLF in a pregnant woman's serum. Generally speaking, the antibodies can be employed in any type of immunoassay in which the result is quantifiable. This includes both single site and two-site, or sandwich assays of the non-competitive type, as well as in traditional competitive binding assays.

Particularly preferred, for ease of detection, is the sandwich assay, of which a number of variations exist, all of which are intended to be encompassed by the present invention.

For example, in a typical forward assay, unlabeled antibody is immobilized on a solid substrate and the sample to be tested brought into contact with the bound molecule. After a suitable period of incubation, for a period of time sufficient to allow formation of an antibody-antigen binary complex. At this point, a second antibody, labelled with a reporter molecule capable of inducing a detectable signal, is then added and incubated, allowing time sufficient for the formation of a ternary complex of antibody-antigen-labeled antibody. Any unreacted material is washed away, and the presence of the antigen is determined by observation of a signal, or may be quantitated by comparing with a control sample containing known amounts of antigen. Variations on the forward assay include the simultaneous assay, in which both sample and antibody are added simultaneously to the bound antibody, or a reverse assay in which the labelled antibody and sample to be tested are first combined, incubated and added to the unlabelled surface bound antibody. These techniques are well known to those skilled in the art, and the possibility of minor variations will be readily apparent. As used herein, "sandwich assay" is intended to encompass all variations on the basic two-site technique.

For the immunoassays of the present invention, the only limiting factor is that the labelled antibody be a PLF-specific antibody. Thus, a number of combinations are possible. The bound antibody and the labelled antibody can both be PLF specific; alternately, the bound antibody will be a non-PLF, specific antiferritin antibody and the second labelled antibody will be PLF specific.

As a more specific example, in the typical forward sandwich assay, a non-PLF specific antiferritin antibody is either covalently or passively bound to a solid surface. The solid surface is usually glass or a polymer, the most commonly used polymers being cellulose, polyacrylamide, nylon, polystyrene, polyvinyl chloride or polypropylene. The solid supports may be in the form of tubes, beads, discs or microplates, or any other surface suitable for conducting an immunoassay. The binding processes are well-known in the art. Following binding, the polymer-antibody complex is washed in preparation for the test sample. An aliquot of the serum sample to be tested is then added to the solid phase complex and incubated at 25° C., for a period of time sufficient to allow binding of any ferritin present to the antibody. The incubation period will vary, but will generally be in the range of about 2 minutes–16 hours. Following the incubation period, the antibody-ferritin solid phase is washed and dried, incubated with a second antibody specific for placental ferritin. The second antibody is linked to a reporter molecule, the visible signal of which is used to indicate the binding of the second antibody to any PLF in the sample. By "reporter molecules", as used in the present specification and claims, is meant a molecule which by its chemical nature, provides an analytically detectable signal which allows the detection of PLF-bound antibody. Detection must be at least relatively quantifiable, to allow determination of the amount of PLF in the sample, this may be calculated in absolute terms, or may be done in comparison with a standard (or series of standards) containing a known normal level of PLF.

The most commonly used reporter molecules in this type of assay are either enzymes, fluorophores or racionuclide containing molecules. In the case of an enzyme immunoassay an enzyme is conjugated to the second antibody, usually by means of glutaraldehyde or periodate. As will be readily recognized, however, a wide variety of different ligation techniques exist, which are well-known to the skilled artisan. Commonly used enzymes include horseradish peroxidase, glucose oxidase, β-galactosidase and alkaline phosphatase, among others. The substrates to be used with the specific enzymes are generally chosen for the production, upon hydrolysis by the corresponding enzyme, of a detectable color change. For example, p-nitrophenyl phosphate is suitable for use with alkaline phosphatase conjugates; for peroxidase conjugates, 1,2-phenylenediamine or tolidine are commonly used. It is also possible to employ fluorogenic substrates, which yield a fluorescent product rather than the chromogenic substrates noted above. In all cases, the enzyme-labelled PLF-specific antibody is added to the first antibody-ferritin complex, allowed to bind to the complex, then the excess reagent is washed away. A solution containing the appropriate substrate is then added to the tertiary complex of antibody-PLF-labelled antibody. The substrate reacts with the enzyme linked to the second antibody, giving a qualitative visual signal, which may be further quantitated, usually spectrophotometrically, to give an evaluation of the amount of PLF which is present in the serum sample.

Alternately, fluorescent compounds, such as fluorescein and rhodamine, may be chemically coupled to antibodies without altering their binding capacity. When activated by illumination with light of a particular wavelength, the fluorochrome-labelled antibody absorbs the light energy, inducing a state of excitability in the molecule, followed by emission of the light at a characteristic longer wavelength. The emission appears as a characteristic color visually detectable with a light microscope. As in the EIA, the fluorescent labelled PLF-specific antibody is allowed to bind to the first antibody-ferritin complex. After washing off the unbound reagent, the remaining ternary complex is then exposed to light of the appropriate wavelength, and the fluorescence observed indicates the presence of interest. Immunofluorescence and EIA techniques are both very well established in the art and are particularly preferred for the present method. However, other reporter molecules, such as radioisotopes, chemiluminescent or bioluminescent molecules may also be employed. It will be readily apparent to the skilled artisan how to vary the procedure to suit the required use.

The present immunoassays are quite useful in detection of abnormal PLF levels as early as the start of the second trimester of pregnancy, i.e., about 12 weeks. The immunoassay may even be extended to detect the presence or absence of PLF in earlier stages of pregnancy, given a suitably sensitive reporter molecule system. The diagnosis of a potentially pathological pregnancy depends on measurement of the amount of detectable PLF in the patient's serum, and correlation of the reading with the standards of PLF levels which are known to be normal for the patient's particular stage of pregnancy. A graphic depiction of the typical pattern of rise and fall of PLF in a normal pregnancy is shown in FIG. 1. More specifically, a PLF level of about 20±15 U/ml may be considered normal for a woman in her twelfth week of pregnancy while a level of 40±25 U/ml will be about normal for the twentieth week.

5.2. FERRITIN-BEARING LYMPHOCYTES

While the aforementioned assays, which detect PLF levels in serum, are quite useful for identifying high risk patients in the second and third trimesters of pregnancy, the levels of PLF in the first trimester can be so low, even in normal pregnant individuals, as to make diagnosis on this basis less than completely reliable. However, it has now been discovered that it is possible to make an accurate etermination of the level of immunosuppression by bservation of the numbers of ferritin-bearing lymphocytes (FBL's) found in the blood of the individual to be tested. Initial studies indicate that immunosuppressed individuals can also be identified by the presence of this specific subset of T-lymphocytes which will react with a PLF-specific monoclonal antibody. These cells carry a PLF-receptor, and bind with PLF in the serum. Such cells are present at a level of at least about 5%, and up to about 20% or more, of all lymphocytes of a normal pregnant individual, but constitute a very low level, usually less than 1%, of the lymphocytes of a normal individual. Although not yet conclusively shown, it appears that expansion of this subset early in pregnancy or even prior to pregnancy, is a prerequisite to the establishment of an immunosuppressed state. Cells of this type have also been observed to occur in high proportions in other disease states in which immunosuppression is a factor in pathology, i.e., breast cancer, Hodgkins disease, and AIDS. Thus, the absence of cells which do not stain when treated with anti-PLF antibody early in pregnancy, i.e., the first trimester, is indictive of a failure of initiation or breakdown of the mechanism necessary to permit the development of an immunosuppressed state. The identification of these cells makes it possible to evaluate levels of PLF-production at a stage in which the level is too low to be detected in serum, but will show up on isolated, anti-PLF antibody-labelled cells. Testing of individuals in the early stages of pregnancy, i.e., the first trimester, for a percentage of FBLs over about 5%, therefore provides an indicator of the state of immunosuppression, and low levels, or complete absence, of the FBLs identifies an individual who may be at risk of a problem pregnancy. Identification of this subset may be made by isolation of lymphocytes from the blood of the individual to be tested by known methods, and conducting an immunoassay of the isolated lymphocytes by reaction with labelled PLF-specific monoclonal antibodies.

Without wishing to be bound by a particular theory of operation, the following pattern of development of the immunosuppressed state, at least in connection with pregnancy, is emerging from the data collected in connection with the present invention. The presence of an embryo/fetus in the mother's body exposes the maternal immune system to alloantigens, in the form of the paternal contribution to the fetus. This exposure to alloantigens, for example, HLA antigens of the father, at least initially causes a nonspecific proliferation of all T-cell populations; included among these is a $CD8^+$ subset of T-cells which cells are either cytotoxic, or, more likely, suppressor, cells. It is believed that the cells which stain when exposed to a PLF-specific antibody represent expanded suppressor cell populations. In a normal pregnancy, the placenta will produce placental isoferritin (PLF) which acts as a "signal" to the suppressor T-cell population to continue proliferation. The suppressor cells have the effect generally of preventing the activity of helper T-cells, and cytotoxic cells. Thus, the suppressive effect of these cells aids in preventing the rejection of the fetus in a normal pregnancy. In a problem pregnancy, however, the immunosuppressive mechanism fails; either the suppressor T-cell population does not proliferate sufficiently, or the placenta does not produce adequate levels of PLF, or both. There is thus no protection afforded to the fetus by way of suppression of the mother's immune system, and the danger of rejection is great. Ultimately the unsuppressed action of the mother's immune system may cause premature labor or even spontaneous abortion.

5.3. IMMUNOSUPPRESSION THERAPY
5.3.1. PLF THERAPY AND PREGNANCY

As noted above, it has often been postulated that the development of certain types of problem pregnancies may be associated with the failure of the pregnant woman to develop a level of immunosuppression which will permit the developing fetus, with its foreign antigens, to coexist safely within the mother's uterus. Beyond this speculation, however, there have been no concrete answers as to the cause of a suppression what should be the normal response of the immune system.

As the foregoing paragraphs and the present examples make clear, there is at the very least a coincidental correlation between very low levels of PLF and several different types of pathological pregnancies, and this correlation provides the basis for a useful marker system. Further examination of the association of PLF with problem pregnancies led to the question of whether there was more than a coincidence involved in the low PLF levels, i.e., whether there was a cause-and-effect association here. In the course of this study, it has now been unexpectedly discovered that PLF has immunosuppressive properties, which may indicate that the lack of its production throughout the course of pregnancy may at least partially be responsible for and directly related to a failure to carry a child to full term in some cases.

Figure 7A:
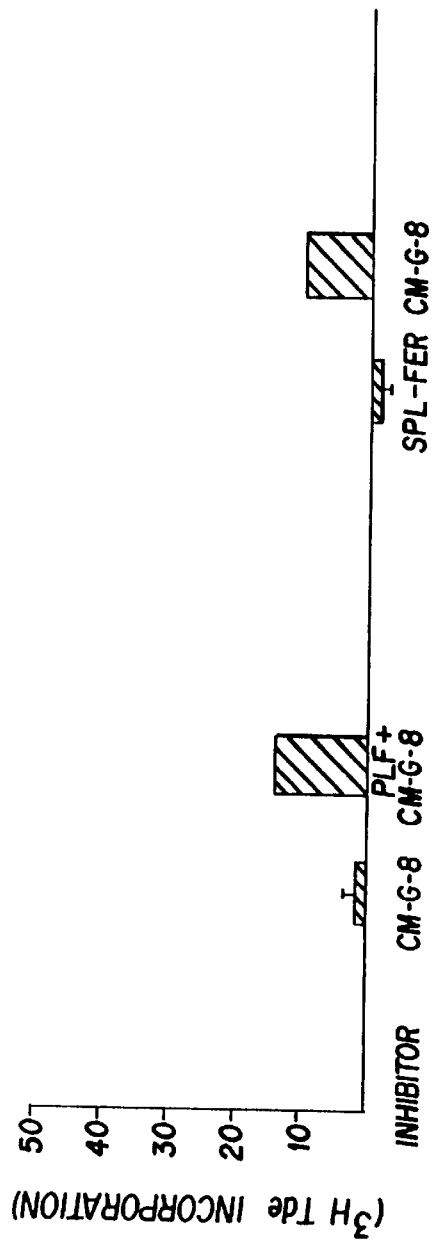
Figure 7B:
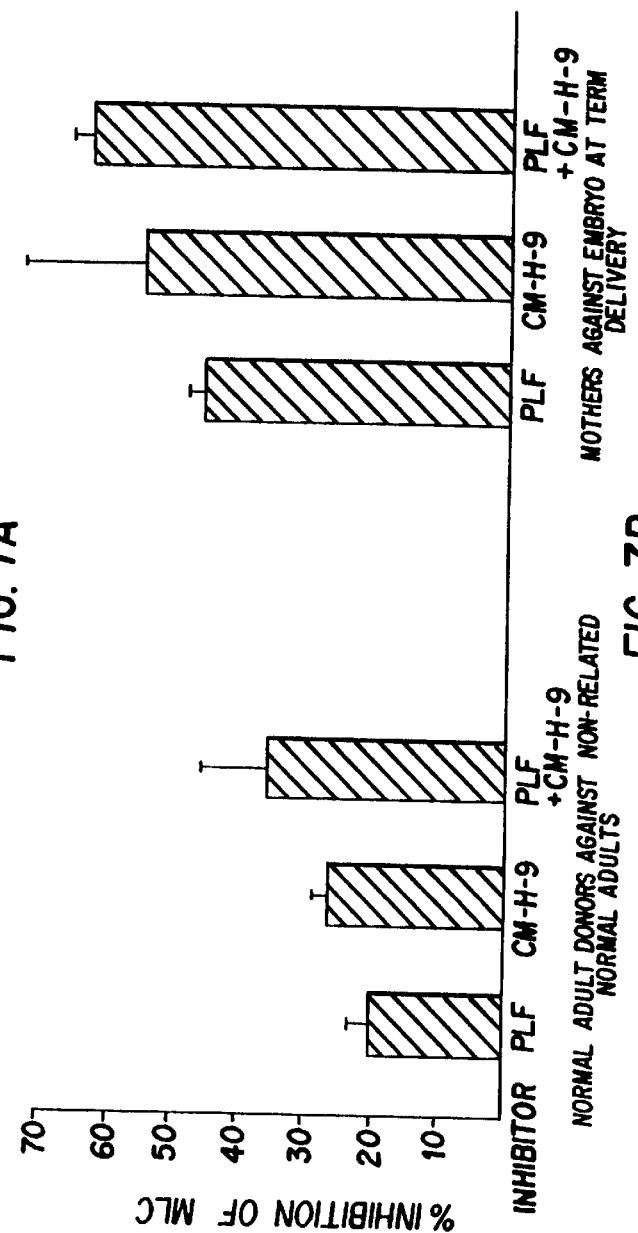

In one-way mixed lymphocyte tests, designed to show the effect a given compound has on the ability of normal lymphocytes to respond to foreign antigens, PLF proved to be quite effective in inhibiting the response of lymphocytes against non-related lymphocytes in culture, as shown in FIG. 7A–7B. In brief, the mixed lymphocyte culture is set up with two different types of unrelated lymphocytes one set of which has been pre-inactivated by treatment with Mitomycin C; under normal circumstances, normal lymphocytes will respond to the presence of a foreign antigen by becoming activated and transferred into lymphoblasts. To test the ability of any given compound to cause immunosuppression, the compound of interest is added to the culture and observations are made on the level of measurable response the functional lymphocytes have against the foreign cells. As shown in FIG. 7A–7B, PLF in culture containing normal donor lymphocytes in the presence of non-related cells did cause a measurable level of inhibition of the expected response. However, the results observed in mixed culture having maternal lymphocytes and cells derived from full term fetus are particularly interesting: cultures in which PLF was placed showed an even greater level of inhibition of maternal vs. embryo response than was observed with normal donor vs. non-related cells. Thus, the presence of PLF has a demonstrated immunosuppressive effect on maternal lymphocytes in the presence of fetal cells. Perhaps more surprising is the marked effect that the PLF-specific antibody has on immunosuppression: the inhibition is even greater than that observed with PLF. Indeed, the response observed with a combination of both PLF and a PLF monoclonal antibody is the highest of all, with over 60% inhibition observed.

The results presented above show the utility of PLF as a useful marker to be detected for diagnostic purposes in problem pregnancies; the apparent immunosuppressive activity of PLF in mixed lymphocyte culture is also strongly indicative of PLF playing an integral role in causing immunosuppression. A third test, however, confirms the role that PLF plays in vivo. one way mixed lymphocyte cultures utilizing matched pairs of mothers and their infants were incubated with the maternal serum presumably containing PLF. Reference to FIG. 10 shows that maternal serum has as strong an inhibitory effect on lymphocyte activity as does PLF added alone to mixed lymphocytes. Even more interesting, however, is the effect of treatment of maternal serum, prior to addition to the MLC, on an immunosorbent column, with CM-H-9, an anti-PLF specific antibody. Again, reference to FIG. 10 shows that, after the removal of PLF from the maternal serum by the antibody, the inhibitory effect of the maternal serum is virtually completely removed. This result supports the conclusion of an active role of PLF in the immunosuppression believed to be necessary in the maintenance of a full term pregnancy.

5.3.2. PLF AND TRANSPLANTS

The immunological similarity between the implantation of an embryo or fetus, and the grafting or transplantation of allogeneic tissue to a host has often been noted. It would be expected that, in both cases, the host immune system would initiate a response against the foreign antigens, and as the ultimate result, rejection of the fetus or the graft would eventually occur. As has already been noted, the induction of an immunosuppressed state at the start of pregnancy is almost certainly responsible for the prevention of embryo rejection; it is also recognized that immune suppression plays a key role in successful transplantation, although in the case of transplants or grafts, immunosuppression is not, apparently, a natural response, as it is in pregnancy. Therefore, it has become routine practice to administer immunosuppressive drugs, such as cyclosporin A, prior to transplantation, in order to "prime" the host's immune system to receive, and more importantly, tolerate, the transplanted tissue.

In recent years, clinical observations have shown that blood transfusions decrease antigen induced and mitogen induced proliferation of the cellular elements associated with immunity, while enhancing suppression activity. In many cases, one or more blood transfusions, prior to transplantation, results in increased tolerance of the allograft, and may minimize rejection of the foreign tissue.

This pattern, at least superficially, resembles the pattern proposed for normal pregnancy as well. It has been suggested that the mechanism of induction of immunosuppression by transfusion is related to an antigen-nonspecific suppression, or idiotypic regulation (Woodruff et al., *Lancet* 1:1201–1203, 1983). More specifically, it is thought that allogeneic lymphocytes present in the transfusion may activate immunosuppression in certain combinations in which the MHC of the blood donor differs from that of the recipient at a particular HLA locus (Shearer et al., *J. Exp. Med.* 157:936–946, 1983).

Based on the physiological similarities between the transplantation and embryo implantation, and the desirability of immunosuppression in each, it is believed that PLF may also serve as a therapeutic agent in prepping a patient for transplantation or grafting, and a regimen is proposed whereby the necessity for transfusion, particularly multiple transfusions, is avoided. It has been observed, however, that PLF alone will not be sufficient to cause inhibition of lymphocyte proliferation. FIG. 11 shows the effect of PLF and anti-PLF antibody on the inhibition of phytohemaglutinnin (PHA) transformation of lymphocytes, prior to transfusion. The same figure, however, shows that, after transfusion, both PLF and the antibody have a significant effect on lymphocyte inhibition. Thus, a combination of PLF infusion and immunization with alloantigens is proposed as an alternative to the currently used drug therapy, which may have undesirable side effects.

5.3.3. THERAPEUTIC REGIMENS

The aforementioned results strongly indicate the therapeutic value of PLF, and the anti-PLF antibody in maintaining a desirable level of immunosuppression in those circumstances in which a hyporeactive immune state is required. It is also shown that PLF probably requires the presence of a particular subject of (presumed) suppression T-cells in order to exert its desired effect, while the cells cannot maintain the suppressed state without the PLF present in the serum as a "signal" for continued proliferation. The observation of these interrelationships suggests a valuable method of inducing the necessary response where the body's natural response is inadequate. In pregnancy, for example, a woman testing negatively, by way of the FBL test, in the first trimester, may be stimulated by immunization with any alloantigen; particularly favored, however, is the use of allogeneic lymphocytes, to initiate or supplement the proliferation of suppressor T-cells. This type of treatment has frequently been used to monitor the effect of exposure of pregnant females to paternal antigens and any resulting effect it may have on a normal term pregnancy (see, e.g., Netter, et al., *Contracept. Fertil. Sex* 15:542–549, 1987; Mowbray et al., *Lancet* 1:941–943, 1985). Immunization with about $10^6$–$10^8$ cells is typically sufficient to provoke a T-cell response. The immunization is followed by parenteral administration of PLF, or a PLF-specific antibody, preferably by infusion. Therapeutic administration of PLF and/or the PLF antibody may range from 1–100 mg, with about 1–10 mg being a preferred range. The patient can then be monitored periodically by ELISA for her serum PLF levels, and, if necessary, boosting doses of PLF/antibody may be administered as needed. For women in the second and third trimesters, an immunization is not usually necessary, since pregnancy.would not continue to this point had an initial level of suppression not already been established. Therefore, the same parenteral administration as noted above is generally adequate to maintain the necessary levels throughout pregnancy to delivery. This can be verified, however, by a simple ELISA to detect the presence of adequate numbers of FBLs.

With respect to pretreatment for transplantation purposes, the individual should be immunized, again with alloantigens, as noted above, preferably at least about 6 days prior to the proposed transplant. The immunization will be followed by PLF and/or antibody infusion preferably within 24 hours of immunization. Following transplantation, PLF levels should be monitored and kept at a level of at least about 20 U/ml. Again, as with pregnancy PLF levels can be readily monitored and boosting doses administered as necessary.

6. EXAMPLE
6.1. PREPARATION OF MONOCLONAL ANTIBODIES

The following protocol describes the method of preparation of both a PLF-specific monoclonal antibody and a ferritin-specific, but non-PLF-specific, monoclonal antibody.

6.1.1. PREPARATION OF ONCOFETAL FERRITIN

Ferritin was prepared from human placenta by a modification of the method used by Beamish et al. (*J. Clin. Path.* 24:581, 1971). Placental tissue (500 gms) was sliced and water added to a total volume of 2000 ml. After homogenization the tissue suspension was heated to 75° C. for 20 minutes. The supernatant, after cooling and centrifugation at 10,000 rpm for 15 minutes, was treated with acetic acid to bring the pH to 4.6. The precipitated protein was removed by centrifugation at 10,000 rpm for 15 minutes and a clear supernatant was adjusted to neutral pH with dilute NaOH. When the clear brown supernatant was ultracentrifuged at 100,000 g for 240 minutes the suspended ferritin collected in a small button at the bottom of the tube. The precipitate was redissolved in 0.9% saline and further purified by passage through a Sephadex G200 column. The ferritin fraction from this column was passed through a DEAE cellulose anion exchange resin using Tris-HCl buffer at pH 7.5 and a 0.02–0.5M gradient. Three protein peaks were obtained, the most acidic peak pI=4.8(No.III) was collected and used for analysis. Its purity was shown by isoelectric focusing and immunoelectrophoresis against anti-ferritin serum and anti-human whole serum. This was used for the immunization of mice, as described below.

6.1.2. PREPARATION OF NON-PLF SPECIFIC HYBRIDOMAS

The myeloma cells used for hybridization were from cell line PB/NS1/1-Ag4-1; these were grown in RPMI-1640 with 20% Fetal Calf Serum (FCS). Spleen cells were obtained from 4–6 week old Balb/c female mice. These mice were immunized with 3 weekly immunizations, of 50 μg of acidic ferritin in complete Freund's adjuvant. Hybridization was begun 3 days after the last injection of 10 μg ferritin. Hyperimmune mice were rested at least one month before the last boosting.

Spleens were removed from the immunized mice in RPMI-0, and rinsed twice in a petri dish with RPMI-0. The spleens were teased apart in RPMI-0 with 18 ga. needles, and the resulting cell suspension transferred to a tube, wherein large chunks of tissue settled out. This single cell suspension was removed to a new tube spun at 800 RPM (160×g) for 5 minutes, and red blood cells were lysed with 0.83% $NH_4Cl$, at pH 7.5. The cells were washed three times with RPMI-0, resuspended in same and counted with Trypan Blue.

The myeloma cells were removed from culture flasks with gentle pipetting into a 50 ml Falcon/Corning tube, and spun down at 900 RPM (200×g) for 5 minutes. They were then washed once with RPMI-0, resuspended in same, and counted with Trypan Blue.

The spleen and myeloma cells were combined in a 10:1 ratio in a single 50 ml conical Falcon/Corning disposable centrifuge tube, and the cells were pelleted at 900 RPM (200×g) for 5 minutes; the medium was aspirated as completely as possible. All solutions and media used from this point were at room temperature. The tube with the cell pellet was immersed in a bath at 37° C., and 0.2 ml 33% PEG 1500 was added for 1 minute, accompanied by gentle stirring and then centrifuged at 200×g for 5 minutes. Cells were resuspended and stirred gently for 1 minute followed by the addition of 5 ml RPMI-0, with gentle stirring and then by addition of of 5 ml RPMI-0, and 20% Fetal Calf Serum. The hybrid mixture looked like a poorly resuspended cell suspension at this point, with many small clumps. The mixture was pelleted at 200×g 5 minutes, and the cells then resuspended in RPMI-HY-HATD (at 37° C.) at a concentration of $3 \times 10^6$/cc by squirting medium onto the cell pellet.

The hybrids were then plated out in flat bottom 96 well plates by adding 2 drops of cell suspension from a 5 ml pipet or with multi-pipettor using cut off tips (about 65 microliters), containing 100–120 RPMI-HY-HATD (approx. $2 \times 10^5$ cells). Control wells containing NS-1 cells+RPMI-HY-HATD at $1 \times 10^6$/ml were set up. Plates were cultured for 7 days. On day 8 and twice a week therefrom, half of the culture medium was removed by careful aspiration and fed with 80–100 microliters of RPMI-HY-HT medium. Positive wells were screened for antibody production at 3 and 4 weeks after hybridization.

The solutions and media used above are prepared in the following manner:
RPMI-0: no RPMI with Fetal Calf Serum RPMI 1640-HY
500 ml sterile distilled water
55 ml 10×RPMI-1640
6 ml 1.0N Sodium Hydroxide
14 ml 7.5% Sodium Bicarbonate $\left.\begin{array}{l}\text{6 ml Pen/strep}\\ \text{10 ml Glutamine}\\ \text{86.5 ml FCS}\end{array}\right\}$ + DMEM RPMI-HY-HATD—day 0 →day 7 For 100 ml of medium
95 ml RPMI-1640+20% FCS
1.0 ml Pyruvate (100×)
2.0 ml 50×HAT
2.0 ml 50×deoxycytidine
RPMI-HY-HT—day 8 →day 14 For 100 ml of medium
97 ml RPMI-1640+20% FCS
2.0 ml 50×HT
1.0 ml Pyruvate (100×)
For Hybrids from day 15 onwards, use RPMI-1640+20% FCS and Pyruvate, or maintain in RPMI-HY-HT.
PEG 33 and 25% w/v Must be odorless and white. For 100 ml autoclave relevant wt in grams in glass bottle at 15 lbs for 10–15 minutes. When bottle is cool enough to hand hold (about 50° C.) add RPMI 1640-0 to make up to 100 ml, swirl to mix, store at room temperature.

| HATD - Final concentrations of reagents | |
|---|---|
| H = Hypoxanthine | $10^{-4}$M |
| A = Aminopterin | $10^{-6}$M |
| T = Thymidine | $2 \times 10^5$M |
| D = Deoxycytidine | $2 \times 10^6$M |

HT Stock 100×—100 cc
Thymidine M.WT 242.33–0.04846 g
Hypoxanthine M.Wt 136.2–0.1361 g dd $H_2O$ up to 100 ml and warm to 60°–70° C. to dissolve.
Readjust final volume with dd $H_2O$. Dilute to 50× and filter (0.2µ) sterilize. Make 2 ml aliquots, store at −20° C.
A Stock 1000×—100 cc
Aminopterin F.Wt 440.4 (0.44 g)
Bring to 50 ml with dd $H_2O$, add 0.1N NaOH dropwise until aminopterin dissolves. Bring final volume to 100 ml with dd $H_2O$. Adjust volume to 100 ml. Filter (0.2µ) sterilize. Store at −20° C.
D Stock 100×—100 cc
Deoxycytidine M.Wt 227.2 (0.00454 g)
Dissolve in dd $H_2O$, adjust to 100 cc, dilute to 50× stock, filter (0.2µ) sterilize and store at −20° C.
HAT-50×200 ml
Combine 100 ml 100×HT with 10 ml 1000×A+90 ml dd $H_2O$=50×HAT, filter (0.2µ) sterilize, make 2 ml aliquots and freeze at −20° C.

Screening and determination of the specificity of the monoclonal antibodies was performed by a hemagglutination test. Embryonic placenta and adult spleen ferritin were coupled to ox red blood cells (Ox RBC) by $CrCl_2$. 50 µl of increasing dilutions (starting at 1:10 of hybridoma culture medium supernatant were mixed with 10 µl of adult or embryonic ferritin Ox RBC and hemagglutination determined. Supernatants of clones giving a hemagglutination titer of at least 1:1000 were selected. A clone designated CM-OF-3 was selected. The antibody produced by the clone CM-OF-3 is specific for ferritin and it cross-reacts with both adult and placental ferritin. The monoclonal antibody obtained, CM-OF-3 was used to block the cross-reactive determinants of placental and adult ferritin, in order to produce a different monoclonal antibody, CM-OF-H9, which is directed to a specific fetal determinant of PLF.

6.1.3. PREPARATION OF PLF-SPECIFIC HYBRIDOMAS AND ANTIBODIES

Placental ferritin (PLF) isolated from human placenta, a protein of pI 4.8, was reacted with monoclonal antibodies CM-OF-3 in the following ratio: PLF (90 µg in PBS) was mixed with ascites fluid from BALB/c mouse containing CM-OF-3 antiferritin monoclonal antibodies (10 mg/ml).

The mixture was incubated for 30 min at 37° C. followed by overnight incubation at 4° C. The mixture was centrifuged at 10000 G, the precipitate formed was discarded, and the supernatant was used for immunization. Each BALB/c mouse was immunized with the above supernatant mixed with complete Freund's adjuvant, injected intradermally once a week for 3 weeks. A booster immunization of one-fifth of the above dose was injected intraperitoneally.

After 3 days from boost, mouse spleen was aseptically removed and fusion was performed by incubating $10^8$ spleen cells with $10^7$/P3-NSI/1-Ag4 myeloma cells as set out above in the hybridization procedure and the same subsequent procedures for positive clone identification was followed. Positive clones were also tested against liver and spleen ferritin to confirm a lack of cross-reactivity. Thus a clone designated as CM-OF-H9 was obtained which produces antibodies CM-H-9. A biologically pure culture of the CM-OF-H9 hybridoma has been deposited with the Institute Pasteur C.N.C.M. under Accession No. I-256.

Characteristics of the CM-OF-H9 monoclonal antibodies include: the CM-H9 monoclonal antibody belongs to the IgG class; it does not form precipitates with ferritin, it binds rabbit complement. In the ascitic fluid obtained, the antibody content was about 7 mg per ml. One ml of ascitic fluid binds about 2 mg of embryonic ferritin and none of adult spleen or liver ferritin.

6.2. PLF LEVELS AND PRETERM DELIVERIES

Twenty-five full-term newborns (14 males and 11 females) aged 38–41 weeks of gestation (mean weight 3350±3000 g), 25 preterm newborns (12 males and 13 females) aged 26–36 weeks of gestation (mean weight 1820±503 g) and their respective mothers were examined. The gestational age was calculated from the first day of the mother's menstrual bleeding preceding pregnancy and was confirmed by clinical examination (Dubowitz scoring). Twenty-three women at 17–22 weeks of gestation who underwent amniocentesis because of their age and fifteen women at 30–39 weeks of normal pregnancy were investigated. Forty healthy volunteers (16 females and 24 males) aged 20–40 years served as controls.

Blood was withdrawn from the umbilical cord of preterm and full-term newborns after ligation of the cord from the newborn side of the placenta. Concomitantly venous blood was obtained from the respective mothers. Amniotic fluid was withdrawn from pregnant women at 17–22 weeks of pregnancy and venous blood was collected from all other groups as shown in Table 1.

Monoclonal antibodies CM-G-8 and CM-H-9 were produced against human placental ferritin as previously described (Moroz et al., 1985). Antibodies were obtained from ascites fluid following precipitation with 50% saturated ammonium sulphate solution. Placental ferritin used for standard was obtained following purification on DEAE-cellulose column as described previously (Moroz et al., *Clin.*

Chem. Acta 148:111, 1985). Liver ferritin standards were obtained from McELISA ferritin kits (Elias Medizin-technik GmbH, D-7800, Freiburg). The amount of placental ferritin which bound 250 pg of alkaline phosphatase-conjugated CM-H-9 MoAb was considered as 10 units of PLF.

The enzyme-linked immunosorbent assays measuring the serum ferritin and PLF in the serum (MoELISA type A and MoELISA type B respectively) have been described (Moroz et al., Exp. Hemat. 15:258, 1987). In both assays, the monoclonal antibody CM-G-8 which binds to all ferritins was coupled to the solid phase. For the second site CM-G-8 MoAb-enzyme conjugate was used in MoELISA type A and CM-H-9 MoAb-enzyme conjugate in MoELISA type B.

The MoELISA type A and B were performed as follows: The wells of a microtitre plate (Dynatech m-129B) were coated with 150 μl CM-G-8 MoAb (100 μg/ml phosphate-buffered saline (PBS), pH 7.2) and incubated overnight at 4° C. The plate was washed three times with PBS-Tween (PBS, 0.05% Tween 20) and shaken dry.

Test sera (100 μl) diluted 1:2 in MoELISA type A and 1:4 in MoELISA type B in PBS-Tween 0.025%, were added in duplicates to the wells. Serum diluent and ferritin standards were also added in duplicates to the wells. Serum diluent and ferritin standards were also added in duplicates. A serum sample with an elevated ferritin concentration was diluted in the diluent to determine recovery at high dilution. The plates were incubated at 4° C. for 1 h in MoELISA A and overnight in MoELISA B, washed three times with PBS-Tween and then 100 μl of alkaline phosphatase (AP) MoAb conjugate (0.4 μl) was added to each well. The plate was incubated further for 120 min at room temperature and washed again three times. The enzyme substrate (p-nitrophenylphosphate 1 mg/ml of diethanolamine buffer, pH 8.0, 0.5 mM $MgCl_2$) was added and the reaction was stopped after 10–30 min by addition of 0.05 ml of 2M NaOH. The amount of colored product was measured by absorbance at 405 nm.

Statistical analysis was performed according to the Mann-Whitney U-test (non-parametric).

The mean concentration of total serum ferritin in pregnant women and in women at delivery was similar to that measured in the sera of adult blood bank female donors (Table 1). The mean concentration of ferritin ranged from 46 to 63 ng/ml as determined by MoELISA type A (Table 1). In comparison, pregnant women exhibited elevated serum concentration of PLF, as measured by MoELISA type B significantly higher than controls (P=0.025, Table 1). It is noteworthy that 70% of the sera of the normal female tested contained no detectable PLF.

In this study it was found that high PLF levels were detected in the serum of women as early as 17 weeks of gestation (45.5±52.9 u/ml). PLF levels did not change significantly during 30–39 weeks of gestation (81.6±89.3) and were high at full-term delivery (54.8±53). However, in women who had preterm delivery the concentration of serum PLF was significantly lower (15.8±15.7 u/ml) than that measured in the sera of pregnant women at similar gestation period and in women at term delivery (P=0.02) (Table 1). Measurement of ferritin concentrations in the amniotic fluid at 17–22 weeks of gestation revealed that the total ferritin concentration (86.4±78.5 ng/ml) was not significantly different from that of the serum (63.7±48.9 ng/ml) whereas the PLF level (19.4±8.2 u/ml was significantly lower than that measured in the serum (45.5±52.9 u/ml, P=0.02).

TABLE 1

The Levels of Ferritin and PLF During Pregnancy

| Female blood donor | n | Ferritin (ng/ml) | PLF (u/ml) |
|---|---|---|---|
| Adult females | 16 | 50.3 ± 59.8 | 4.5 ± 7.7 |
| Pregnant 17–22 weeks | 23 | 63.7 ± 48.9* | 45.5 ± 52.9† |
| Pregnant 30–39 weeks | 15 | 50.0 ± 39.4* | 81.6 ± 89.3† |
| Term delivery | 25 | 46.1 ± 37.3* | 54.8 ± 53.0† |
| Preterm delivery | 18 | 61.2 ± 29.4* | 15.8 ± 15.7†⁺ |
| Amniotic fluid 17–22 weeks | 15 | 86.4 ± 78.5 | 19.4 ± 8.2 |

*Not significantly different from adult female.
†Significantly higher than adult female (P = 0.0025).
⁺Significantly lower than in pregnant women and women at term delivery (P = 0.02).
The results are expressed as mean ± s.d.

Determinations of ferritin and PLF in the sera of term and preterm newborns. The mean concentration of total ferritin in the sera of full-term and preterm newborns (289.4±167.5, 208.2±191.5 respectively) was significantly higher than that measured in the sera of their mothers (46.1±37.3, 61.2±29.4 respectively, P=0.0005, Table 2). Yet no difference in serum ferritin concentration was observed between term and preterm newborns (Table 2).

High PLF levels were detected in the sera of term newborns (20.3±25.8 u/ml) as compared to normal healthy adults (8.1±14.8 u/ml). However, the levels of PLF were significantly lower than that of their mothers (Table 2, P=0.0075). In contrast in preterm newborns the serum PLF levels (9.4±15.1) were low, similar to those of healthy adults but were significantly lower than those of their mothers (P=0.018). The PLF levels in preterm newborns were not significantly lower than those found in term newborns (P=0.26).

TABLE 2

The Levels of Ferritin and PLF in the Sera of Full-term and Preterm Newborns and Their Mothers.

| Group | n | Ferritin (ng/ml) | PLF (u/ml)* |
|---|---|---|---|
| Full term newborns | 25 | 289.4 ± 167.5 P = 0.0000 | 20.3 ± 25.8 P = 0.0075 |
| Mothers | 25 | 46.1 ± 37.3 | 54.8 ± 53.0⁺ |
| Preterm newborns | 25 | 208.2 ± 191.5 P = 0.0005 | 9.4 ± 15.1 P = 0.018 |
| Mothers | 18 | 61.2 ± 29.4 | 15.8 ± 15.7 |
| Blood bank donors | 40 | 85.3 ± 65.9 | 8.1 ± 14.8 |
| Male | 24 | 108.0 ± 58.0 | 10.0 ± 10.0 |
| Female | 16 | 50.3 ± 59.8 | 4.5 ± 7.7 |

*The results as mean ± s.d.
⁺Significantly higher than PLF in the sera of mothers of preterm newborns and adult female (P = 0.02, P = 0.0025 respectively).

6.3. PLF LEVELS AND TOXEMIA OF PREGNANCY

Twenty patients with toxemia of pregnancy (PET) who delivered their babies in the mid to late third trimester, were selected prospectively on the basis of standard clinical criteria. None of these women had eclampsia. Five women had severe pre-eclampsia, two had gestational diabetes with mild PET, one had chronic hypertension with superimposed PET the rest of the women had mild PET (see Table 1). All the patients in the two control groups had normal uncomplicated pregnancies and deliveries.

Blood for chemical analysis was drawn into glass collection tubes. Serum was collected into glass tubes, immediately frozen and stored at −20° C. until analyzed. Total serum ferritin was measured independently in two different laboratories. One used a monoclonal antibody ELISA method. The second laboratory used a polyclonal antiserum ELISA. The anti-human ferritin-enzyme conjugate was obtained from DAKO and ferritin standards were obtained from serono diagnostics. The results obtained from these two laboratories were compatible. The measurement of the serum PLF was performed by a MoELISA as previously described.

Statistically analysis was performed using T test for unpaired observations. Differences were considered significant at $p<0.05$.

Table 3 exhibits the clinical data of the 20 PET patients. It is noteworthy that the mean gestational week of the toxemic patients was 36±3.2 The haemoglobin level ranged between 8.8 to 13.9 gr % with a mean of 11.3±1.45 gr %.

TABLE 3

Clinical Data of the Pre-Eclamptic Toxemia Group (N = 20)

| | N | Range | Mean | S.d. |
|---|---|---|---|---|
| Maternal age (years) | 20 | 22–38 | 30 | 5.25 |
| Primipara | 12 | | | |
| Multipara | 7 | | | |
| Grand Multipara | 1 | | | |
| Gestation age (weeks) | 20 | 29–42 | 36 | 3.2 |
| Oedema | 120 | | | |
| Albuminuria (1–4+) | 20 | | | |
| Haemoglobin (9%) | 20 | 8.8–13.9 | 11.35 | 1.45 |
| Systolic B.P. (on admittance) | 20 | 130–200 | 153 | 19 |
| Diastolic B.P. (on admittance) | 20 | 80–110 | 98 | 10.7 |
| Gest. diabetes | 2 | | | |
| Chronic hypertension and superimposed PET | 1 | | | |
| Mode of delivery | | | | |
| C/S | 7 | | | |
| Vag. | 13 | | | |
| Birth weight in grams | 20 | 700–3700 | 2676 | 800 |
| Ante-partum fetus death | 1 | | | |

The mean serum concentration of normal ferritin in toxemic patients was 38.55±55 (ng/ml). This level was not significantly different from that level found in normal pregnant women at 30–39 weeks of gestation (50.0±39.4 ng/ml) or from the mean serum level in normal women at term delivery (46.1±37.3 ng/ml) (FIG. 8).

As seen in FIG. 9, the mean PLF level in the sera of toxemic patients was 7.5±23 u/ml. This level was significantly lower ($p<0.001$) than the level of PLF (81.6±89.3) in normal pregnant women at similar gestational age (30–39 weeks) as well as from the level of PLF measured in women at normal term delivery (54.8±53 u/ml). It is noteworthy that 17/20 toxemic patients were completely lacking PLF in their serum and only 1/20 had a PLF level compatible with the level observed in the normal pregnancies of similar gestational age.

What is claimed is:

1. A method of reducing the incidence of spontaneous abortion, preeclamptic toxemia, preterm labor, or preterm delivery in a mammal comprising the administration of a therapeutic amount of PLF.

2. A method of inducing spontaneous abortion, preeclamptic toxemia, preterm labor, or preterm delivery in a mammal comprising the administration of a therapeutic amount of an antibody which neutralizes PLF.

3. The method of claim 1 wherein the amount of PLF is about 1–100 mg.

4. The method of claim 2 wherein the amount of antibody is 1–100 mg.

5. The method of claim 1 wherein, prior to PLF or antibody administration, the mammal has been immunized with an effective amount of alloantigens.

6. The method of claim 5 wherein the alloantigens are provided in the form of alloantigenic lymphocytes.

7. The method of claim 2 wherein the antibody has the identifying characteristics of CM-H-9.

8. The method of claim 4 wherein the antibody has the identifying characteristics of CM-H-9.

9. A pharmaceutical composition comprising an immunosuppressive amount of an antibody having specificity for PLF, in combination with a pharmaceutically acceptable carrier.

10. The composition of claim 9 which also comprises an immunosuppressive amount of PLF.

11. The composition of claim 9 or 10 wherein the antibody has the identifying characteristics of CM-H-9.

* * * * *